United States Patent
Oh et al.

[11] Patent Number: 5,736,104
[45] Date of Patent: Apr. 7, 1998

[54] TRANSITION METAL OXIDE BASED CALORIMETRIC NON-METHANE HYDROCARBON SENSOR AND METHOD

[75] Inventors: Seajin Oh; Jose Joseph, both of Palo Alto, Calif.

[73] Assignee: Motorola Inc., Schaumburg, Ill.

[21] Appl. No.: 622,273

[22] Filed: Mar. 27, 1996

[51] Int. Cl.$^6$ ..................................... G01N 27/16
[52] U.S. Cl. .................... 422/96; 422/83; 422/94; 422/95; 422/97; 422/98; 436/133; 436/134; 436/137; 436/141; 436/143; 436/147; 436/149; 436/152; 65/60.5; 65/60.52; 427/126.3; 427/126.6
[58] Field of Search ............... 422/83, 94, 95, 422/96, 97, 98; 436/133, 134, 137, 141, 143, 147, 149, 152; 65/60.5, 60.52; 427/126.3, 126.6

[56] References Cited

U.S. PATENT DOCUMENTS

| | | | |
|---|---|---|---|
| 3,657,691 | 4/1972 | Adachi et al. | 252/465 |
| 4,000,089 | 12/1976 | Senda | 252/514 |
| 4,007,435 | 2/1977 | Tien | 338/34 |
| 4,012,692 | 3/1977 | Eicher | 324/71 SN |
| 4,064,073 | 12/1977 | Pomot | 252/465 |
| 4,142,988 | 3/1979 | Chinchen | 252/373 |
| 4,543,273 | 9/1985 | Handa et al. | 427/126.3 |
| 4,732,736 | 3/1988 | Nakatani et al. | 422/94 |
| 5,271,816 | 12/1993 | Tanaka et al. | 204/153.16 |
| 5,478,528 | 12/1995 | Golonski et al. | 422/88 |

FOREIGN PATENT DOCUMENTS

| | | |
|---|---|---|
| 5-314537 | 11/1993 | Japan . |
| 0103521 | 12/1991 | Romania . |

OTHER PUBLICATIONS

Allan Symons, Catalytic Gas Sensors, 1992, pp. 169–185.

*Primary Examiner*—Jill Warden
*Assistant Examiner*—Sharidan Carrillo
*Attorney, Agent, or Firm*—Nicholas C. Hopman

[57] ABSTRACT

A transition metal oxide based calorimetric non-methane hydrocarbon sensor (100) is constructed by disposing a transition metal based catalyst (105), preferably chromium oxide ($Cr_2O_3$), onto a carrier (101). A temperature measurement device (103) is positioned thermally coupled to the transition metal based catalyst (105). A preferred application includes sensing non-methane heavy hydrocarbons in an automotive exhaust gas stream (803) by exposing a transition metal oxide catalyst based sensor (805) to the exhaust gas stream (803) and providing a signal (811) indicative of a concentration of non-methane heavy hydrocarbons and carbon monoxide (CO). Then, exposing a compensating sensor (807) to the same exhaust gas stream (803) and providing a compensating signal (813) indicative of a concentration of carbon monoxide (CO). By combining the signal (811) and the compensating signal (813), a measure of non-methane heavy hydrocarbons can be provided.

6 Claims, 3 Drawing Sheets

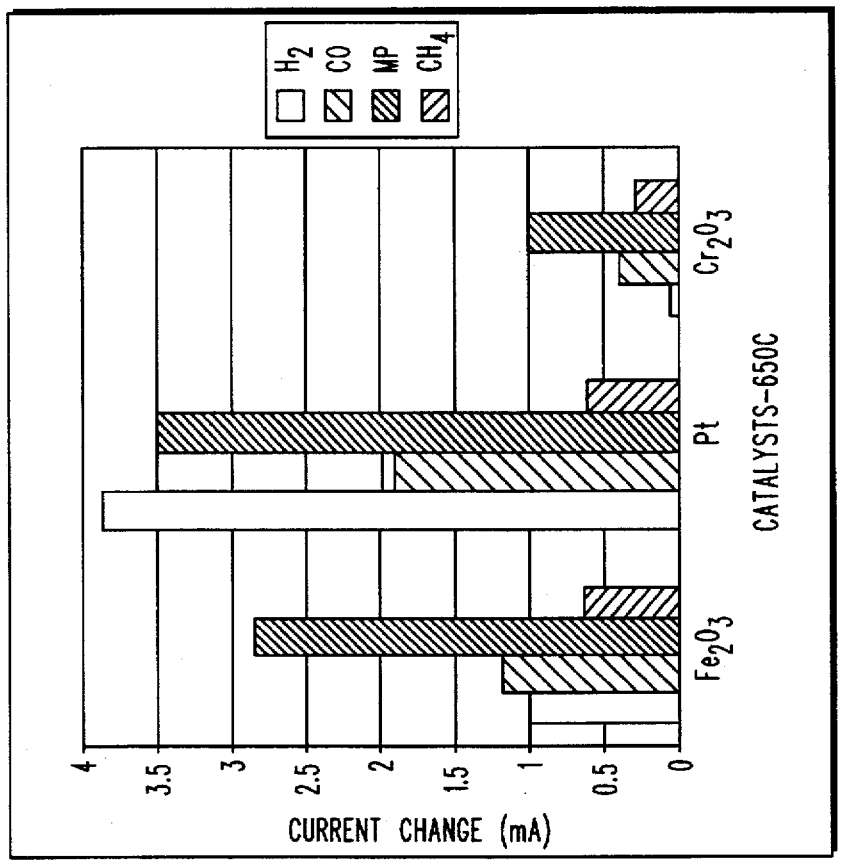

TRANSITION METAL OXIDE BASED CALORIMETRIC NON-METHANE HYDROCARBON SENSOR AND METHOD

FIELD OF THE INVENTION

This invention is generally directed to the field of sensors, and specifically for a calorimetric non-methane hydrocarbon sensor that uses transition metal oxides as a catalyst. In addition to other applications this approach can be useful for determining concentrations of non-methane hydrocarbons in an internal combustion engine's exhaust gas stream.

BACKGROUND OF THE INVENTION

Calorimetric sensors are often employed to measure gas concentration of one gas or a combination of gases. Certain prior art calorimetric sensors are constructed using noble metals as catalysts to determine concentrations of certain gases or groups of gases. The noble metal catalyst promotes oxidation of a combustible gases, or gases to be measured. Oxidation reactions generate heat which causes a rise in temperature proximate the area of the reaction. A resulting increase in temperature can be sensed and used to indicate a concentration of the combustible gas or gases under measure. Because noble metals are expensive, the sensor manufacturing process requires many special precautions including reclamation of the noble metals. Extra process steps add to the complexity and cost of manufacturing. Furthermore, noble metal catalysts are not stable at the relatively high operating temperatures (600° C.–900° C.) of an automotive exhaust gas plenum. The high temperatures cause these noble metals to evaporate, and also to shrink in surface area. Both of these reactions to high temperature cause a loss in sensitivity over the life of the sensor.

As a practical matter, catalysts are rarely specific to a particular gas molecule. As a result, gases other than the one, or group, of interest can cause interference during a measurement. Therefore, the achievement of a reasonable degree of gas molecule selectivity is a major technical hurdle to overcome in sensor design.

An example of this can be seen in application of a hydrocarbon sensor in an automobile exhaust gas plenum. Hydrocarbon sensors in particular are required to measure concentration of nonmethane (or heavy) hydrocarbons in internal combustion engine exhaust gas streams. One basis for this is that environmentally driven emissions legislation is regularly being changed to require lower and lower emissions of pollutants from vehicles. In particular, The California Air Resources Board (CARB) is leading an effort with their OBDII (On-Board Diagnostics II) requirement. OBDII requires detection of emitted hydrocarbons in the 100 PPM (parts per million) range.

In an automotive application, an internal combustion engine produces exhaust comprising hydrogen ($H_2$) and nonmethane hydrocarbons ($Ch_x$), as well as other gases comprising: carbon monoxide (CO), methane ($CH_4$), carbon dioxide ($CO_2$), nitric oxide (NO), and water vapor ($H_2O$). In hydrocarbon sensors using noble metals as a catalyst, it is very difficult to eliminate hydrogen ($H_2$) interference, when other combustible gases such as non-methane hydrocarbons have to be measured selectively.

What is needed is an improved non-methane hydrocarbon sensor that maintains its sensitivity over the operating life of the sensor, is less complex and costly to manufacture, and is less sensitive to interference from other combustible gasses in the exhaust gas stream-in particular hydrogen ($H_2$).

BRIEF DESCRIPTION OF THE DRAWINGS

FIG. 2 is a chart illustrating selectivity of various catalysts when exposed to various gasses at a temperature of 550° C.;

FIG. 3 is a chart showing selectivity of various catalysts when exposed to various gasses at a temperature of 650° C.;

DETAILED DESCRIPTION OF A PREFERRED EMBODIMENT

Figure 1:
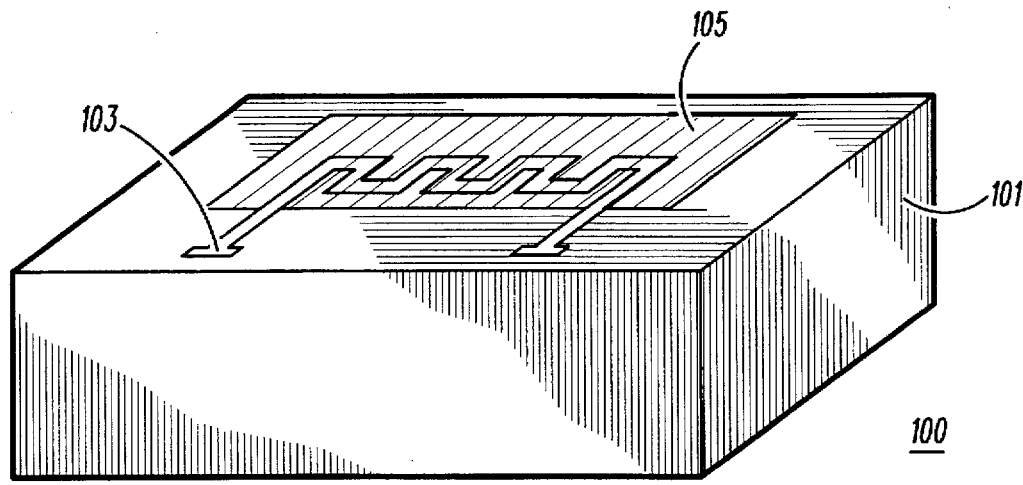
FIG. 1 is a schematic of a transition metal oxide catalyst based planar thermocatalytic sensor in accordance with a preferred embodiment of the invention.

A transition metal oxide based calorimetric non-methane hydrocarbon sensor is constructed by disposing a transition metal based catalyst onto a carrier. A temperature measurement device is positioned thermally coupled to the transition metal based catalyst. A preferred application includes sensing non-methane heavy hydrocarbons in an automotive exhaust gas stream by exposing the transition metal oxide based catalyst to the automotive exhaust gas stream and providing a signal indicative of a concentration of non-methane heavy hydrocarbons and carbon monoxide (CO). Then, exposing a compensating sensor to the same automotive exhaust gas stream and providing a compensating signal indicative of a concentration of carbon monoxide (CO). By combining the signal and the compensating signal, a measure of non-methane heavy hydrocarbons can be provided.

The calorimetric non-methane hydrocarbon sensor employs the transition metal oxide catalyst to oxidize various gases. As mentioned in the Background, the catalyst promotes oxidation of combustible gases to be measured. When the gases react with the transition metal oxide catalyst, the resulting oxidation generates heat which causes a rise in temperature proximate an area of the catalytic reaction. The rise in temperature is sensed by a temperature measurement device and used to indicate a concentration of the gases under measure. Next, various transition metal oxides were tested to determine their usefulness.

To evaluate various catalyst materials bead-architecture sensors were fabricated and tested for sensitivity to $H_2$, CO, heavy hydrocarbons, and $CH_4$. Transition metal oxides tested were titanium oxide ($TiO_2$), vanadium oxide ($V_2O_5$), chromium oxide ($Cr_2O_3$), manganese oxide ($Mn_2O_3$), ferric oxide ($Fe_2O_3$), cobalt oxide ($Co_3O_4$), nickel oxide (NiO), copper oxide (CuO), zinc oxide (ZnO). Other metal oxides tested were $Y_2O_3$-doped $ZrO_2$, and $LaSrCoO_3$. Preparation of the materials was made as follows. Ten grams (g) 0.3-micron alumina powder was mixed with 1 gram of $Al(NO_3)_3$ 9 $H_2O$, approximately 6 grams of metal oxide powder, and 3 drops of glacial acetic acid into 25 milliliter (ml) of deionized water. This mixture was milled for 24 hours. Then, a 10 ml corn starch solution, made by mixing 0.04 g corn starch powder and deionized water, was added and the mixture was milled for 24 hours. A GasTech reference element made of bare alumina was coated with the slurry and fired by powering to at least 700° C.

The results of the testing are given in Table 1.

TABLE 1

| catalysts | coating | sensitivity to | | | | |
|---|---|---|---|---|---|---|
| | | $H_2$ 0.50% | CO 0.50% | MP[a] 0.25% | TMP[b] 0.25% | $CH_4$ 2.50% |
| $TiO_2$ | • | + | + | + | | + |
| $V_2O_5$ | ++[c] | N/A | N/A | N/A | | N/A |
| $Cr_2O_3$ | • | ++ | • | Δ | Δ | + |
| $Mn_2O_3$ | • | • | • | • | | + |
| $Fe_2O_3$ | • | +/++ | • | Δ | Δ | + |
| $Co_3O_4$ | • | • | • | • | | + |
| NiO | • | • | • | • | • | + |
| CuO | • | • | • | • | | + |
| ZnO | • | + | + | + | | + |
| $MoO_3$ | ++[c] | N/A | N/A | N/A | | N/A |
| $Y_2O_3$—$ZrO_2$ | • | + | + | + | | + |
| $LaSrCoO_3$ | + | + | • | • | | + |

[a]Methylpropene
[b]Trimethylpentane
[c]Adhesion was very poor
• good
Δ very good
+ poor
++ very poor At 550° C. and 650° C., $Mn_2O_3$, $Co_3O_4$, NiO, and CuO were selective to $H_2$, CO, and methylpropene nonselectively, while $Cr_2O_3$, $Fe_2O_3$, and $LaSrCoO_3$ were very selective to methylpropene. $Fe_2O_3$ was not selective to $H_2$ at 650° C. but was selective to some extent at 550° C., so its grading in Table 1 is both poor and very poor.

When the bead was coated with $V_2O_5$ and $MoO_3$ slurry and fired, the adhesion of the coated layer was very poor. Recrystallization in the coated film during diring was observed under an optical microscope. A different coating method is required for $V_2O_5$ and $MoO_3$. $TiO_2$, ZnO, and YSZ were not noticeably selective to the test gases.

Most of the metal oxides did not respond to $CH_4$ because the catalyst morphology and coating method were not appropriate for $CH_4$ oxidation. The signal from $CH_4$ was mixed with the background signal and could not be distinguished. Next sensor architectural construction will be detailed.

An improved sensor can be constructed using different architectures. A planar architecture transition metal oxide catalyst based thermocatalytic sensor 100 is illustrated in FIG. 1. A substrate 101 can be constructed using various materials. In the preferred embodiment the substrate is constructed of a ceramic material. Next, a temperature sensing element 103 is disposed onto the ceramic substrate 101. Then, a transition metal oxide catalyst material 105 is disposed onto the temperature sensing element 103. Elements 103 and 105 may be oriented in a different configuration, as long as there is a thermal coupling between them. For example in an alternative architecture commonly referred to as a bead-type architecture, the catalyst is formed in a bead-type geometry surrounding a wire, and the wire is used as the temperature sensing element. Returning to FIG. 1, as gas is exposed to the structure 100, certain gas constituents will oxidize on the transition metal oxide catalyst, 105 causing a rise in temperature of the transition metal oxide catalyst. This rise in temperature is measurable using the temperature sensing element 103. In conclusion, the specific architecture of the sensor is not crucial as long as there is a thermal coupling between the temperature sensing element 103 and the transition metal oxide catalyst material 105, and the temperature of the transition metal oxide catalyst material 105 is maintained at a temperature most optimal to the oxidation process with the particular catalyst materials used. Next, the catalyst properties will be detailed.

As shown above certain transition metal oxides, for example ferric oxide ($Fe_2O_3$) and chromium oxide ($Cr_2O_3$), are sensitive to heavier hydrocarbons ($Ch_x$) and carbon monoxide (CO) while not being very sensitive to hydrogen ($H_2$).

Sensitivity comparisons of ferric oxide ($Fe_2O_3$), chromium oxide ($Cr_2O_3$), and platinum (Pt) catalysts to hydrogen ($H_2$), carbon monoxide (CO), methylpropene, and methane ($CH_4$) are given in FIG. 2 and FIG. 3. Because the signal magnitude greatly depends on the catalyst microstructure, which is determined by the catalyst preparation method, it is not appropriate to compare the absolute values of current change, but the comparison of magnitudes between the gases using the same catalyst is still useful.

Both FIG. 2 and FIG. 3 show that platinum (Pt) was a very active catalyst for hydrogen ($H_2$) and for methylpropene at 550° C. and above. Ferric oxide ($Fe_2O_3$) was selectively sensitive to methylpropene at 550° C., but appeared to lose selectivity at 650° C. Chromium oxide ($Cr_2O_3$) was not selective to hydrogen ($H_2$) at 550° C. or 650° C., and for methylpropene the signal magnitude increased with temperature. Therefore, ferric oxide ($Fe_2O_3$) is more useful for a lower-temperature application, while chromium oxide ($Cr_2O_3$) is more suitable for the higher-temperature application. Note that, both ferric oxide ($Fe_2O_3$) and chromium oxide ($Cr_2O_3$) are selective to carbon monoxide (CO) as well. To selectively measure non-methane hydrocarbons the sensitivity to carbon monoxide (CO) will have to be eliminated and a structure to do so will be detailed later.

Results of durability testing is shown in FIGS. 4–7. The absolute signal magnitude of two sensors is different, as the amount of catalyst applied manually might not be the same. The selectivity of ferric oxide $Fe_2O_3$ to methylpropene degraded to some extent in the first 100 or more hours, but it reached steady state. The selectivity was maintained during the annealing. The as-received chromium oxide ($Cr_2O_3$) sensor gave a low absolute signal, but the magnitude increased during annealing. During 400 hours of annealing, neither sensor selectivity nor selectivity deteriorated noticeably.

Metal oxide catalysts are very attractive because they are inexpensive and durable. The high selectivity to heavy hydrocarbons, methylpropene and trimethylpentane, and low or no selectivity to hydrogen ($H_2$) are very positive aspects of ferric oxide ($Fe_2O_3$) and chromium oxide ($Cr_2O_3$) catalysts. This performance enables the measurement of low concentrations of heavy hydrocarbons. However, because of their response to carbon monoxide (CO), these sensors must be augmented so that the metal oxide catalysts become useful for the selective measurement of heavy hydrocarbons. To accomplish this a second—or compensating sensor is needed. The compensating sensor must be sensitive to carbon monoxide (CO).

By combining the outputs of the transition metal oxide based sensor and a sensor sensitive to carbon monoxide (CO), a sensor that measures heavier hydrocarbons in the presence of hydrogen ($H_2$) and carbon monoxide (CO) can be constructed. Also, by combining the outputs of the transition metal oxide based sensor and a non-active element, a sensor that measures carbon monoxide (CO) and heavier hydrocarbons in the presence of hydrogen ($H_2$) can be constructed.

Figure 8:
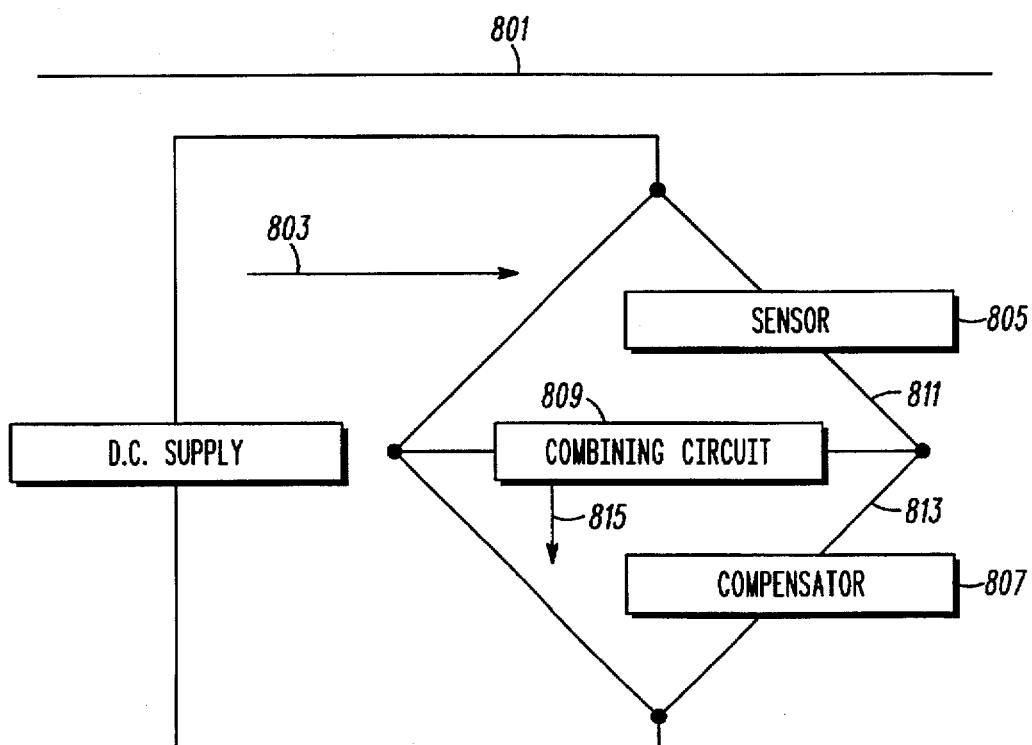
FIG. 8 is a schematic showing a system for measuring carbon monoxide (CO) and/or heavier hydrocarbons in the presence of hydrogen ($H_2$) using the sensor detailed in FIG. 1.
Figure 4:
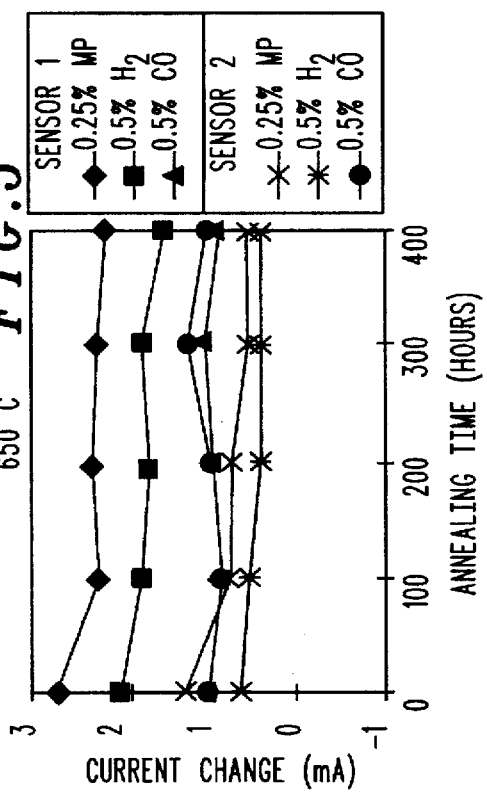
FIG. 4 is a chart illustrating stability of a ferric oxide ($Fe_2O_3$) catalyst after annealing at a temperature of 650° C., when exposed to various gasses at a temperature of 550° C.
Figure 5:
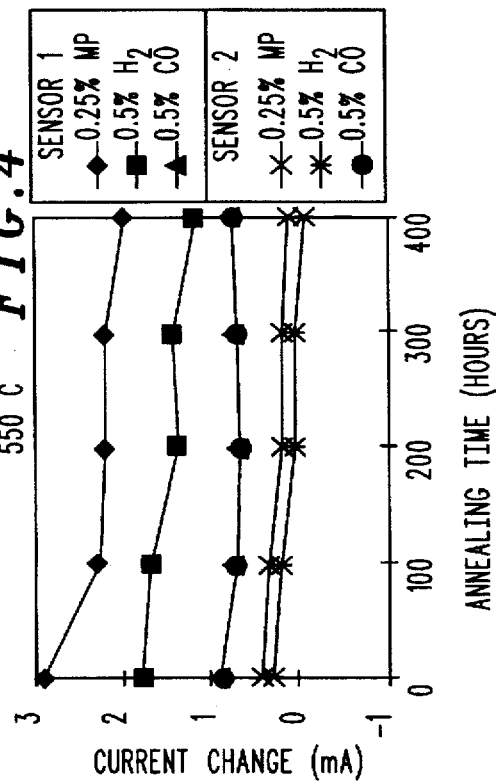
FIG. 5 is a chart showing stability of a ferric oxide ($Fe_2O_3$) catalyst after annealing at a temperature of 650° C., when exposed to various gasses at a temperature of 650° C.
Figure 6:
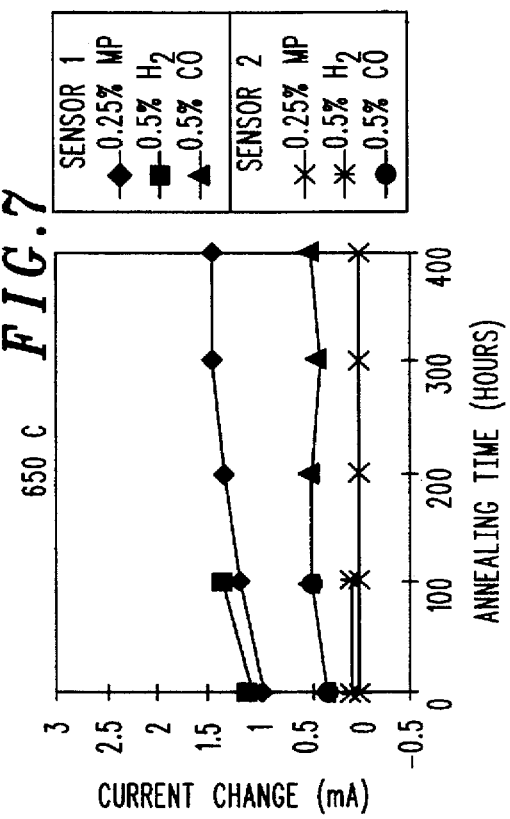
FIG. 6 is a chart illustrating stability of a chromium oxide ($Cr_2O_3$) catalyst after annealing at a temperature of 650° C., when exposed to various gasses at a temperature of 550° C.
Figure 7:
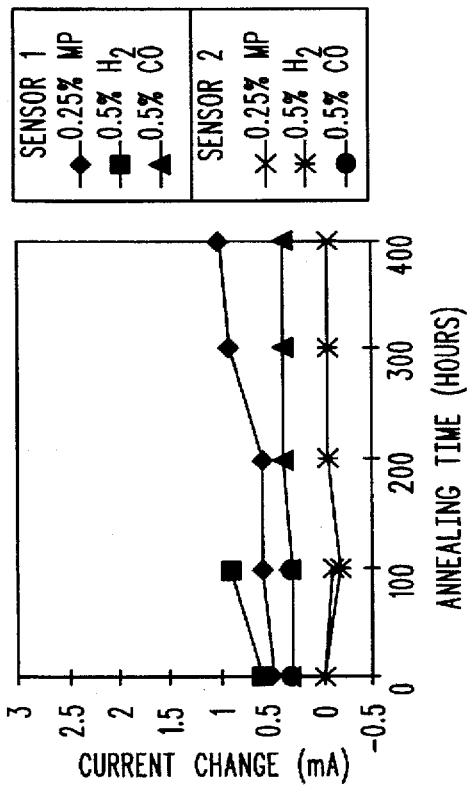
FIG. 7 is a chart showing stability of a chromium oxide ($Cr_2O_3$) catalyst after annealing at a temperature of 650° C., when exposed to various gasses at a temperature of 650° C.

FIG. 8 shows a system for measuring heavier hydrocarbons in the presence of hydrogen ($H_2$) in an automotive exhaust gas stream using the sensor detailed in FIG. 1. A sensor 805, including a transition metal oxide based catalyst, is exposed to the automotive exhaust gas stream 803 in an exhaust gas plenum 801. The sensor 805 and provides a signal 811 indicative of a concentration of non-methane heavy hydrocarbons and carbon monoxide (CO) in the exhaust gas stream 803. A compensating sensor 807 is also exposed to the to the exhaust gas stream 803 and provides a compensating signal 813 indicative of a concentration of carbon monoxide (CO) in the exhaust gas stream 803. The sensors 805 and 807 are combined in a Wheatstone bridge configuration. A combining circuit 809 combines the signals 811 and 813 and provides a ssinal 815 indicative of a measure of non-methane heavy hydrocarbons in the exhaust gas stream 803.

In an automotive exhaust gas application, to properly oxidize the non-methane hydrocarbons, the transition metal oxide catalyst 105 needs to operate within a temperature range proximate 400° C. to 600° C. In an automotive application, the engine's exhaust gas temperature ranges between 600° C. and 900° C. To maintain an optimal reaction to the non-methane hydrocarbon gasses the temperature sensing element 103 may also include a heating and/or a cooling structure.

In conclusion, advantages of the described approach include selective measurement of carbon monoxide (CO) and/or heavier hydrocarbons, in the presence of hydrogen ($H_2$), by using inexpensive transition metal oxides rather than relying exclusively on noble metals such as platinum (Pt). The described sensor can not only maintain its sensitivity over its operating life, but is easier to manufacture than those sensors based on noble metals.

What is claimed is:

1. A sensor for measuring a concentration of non-methane hydrocarbons in an automotive exhaust gas stream comprising:

a carrier;

a chromium oxide ($Cr_2O_3$) catalyst disposed onto the carrier for oxidizing hydrocarbons in the automotive exhaust gas stream;

a temperature measurement device thermally coupled to the chromium oxide ($Cr_2O_3$) catalyst on said carrier for measuring a concentration of non-methane hydrocarbons and carbon monoxide (CO) in the automotive exhaust gas stream and providing an output signal indicative thereof;

a compensating sensor having an output for providing a signal indicative of a concentration of carbon monoxide (CO) in the automotive exhaust gas stream; and a circuit, operatively coupled to the temperature measurement device and the compensating sensor, for combining the output signal of the temperature measurement device with the signal indicative of the concentration of carbon monoxide (CO) in the automotive exhaust gas stream, to produce a signal indicative of the concentration of non-methane hydrocarbons in the automotive exhaust gas stream.

2. A sensor in accordance with claim 1 wherein the chromium oxide ($Cr_2O_3$) catalyst oxidizes the hydrocarbons at a temperature between 400° C. and 600° C.

3. A sensor in accordance with claim 1 wherein the circuit comprises a Wheatstone bridge measurement circuit.

4. A method for manufacturing a non-methane hydrocarbon sensor used to measure a concentration of non-methane hydrocarbons in an automotive exhaust gas stream comprising the steps of:

providing a carrier;

disposing a chromium oxide ($Cr_2O_3$) catalyst onto the carrier for oxidizing hydrocarbons in the automotive exhaust gas stream;

providing a temperature measurement device thermally coupled to the chromium oxide ($Cr_2O_3$) catalyst on said carrier for measuring a concentration of non-methane hydrocarbons and carbon monoxide (CO) in the automotive exhaust gas stream and providing a first output signal indicative thereof;

providing a compensating sensor, the compensating sensor measuring concentrations of carbon monoxide (CO) in the automotive exhaust gas stream and providing a second output signal indicative thereof; and providing a circuit operatively coupled to the temperature measurement device and the compensating sensor for combining the first output signal with the second output signal to produce a signal indicative of the concentration of non-methane hydrocarbons in the automotive exhaust gas stream.

5. A method for measuring a concentration of non-methane hydrocarbons in an automotive exhaust gas stream comprising the steps of:

exposing a transition metal oxide based catalyst to the automotive exhaust gas stream to produce a first signal indicative of a concentration of non-methane hydrocarbons and carbon monoxide (CO);

exposing a compensating sensor to the automotive exhaust gas stream to produce a compensating signal indicative of a concentration of carbon monoxide (CO); and combining the first signal with the compensating signal to produce a signal indicative of the concentration of non-methane hydrocarbons in the automotive exhaust gas stream.

6. A method in accordance with claim 5 wherein the transition metal oxide based catalyst is comprised of a material selected from the group consisting of ferric oxide ($Fe_2O_3$) and chromium oxide ($Cr_2O_3$).

* * * * *